United States Patent
Anai et al.

(10) Patent No.: US 7,067,718 B2
(45) Date of Patent: Jun. 27, 2006

(54) METHOD OF PRODUCING DIACYLGLYCEROL AND GENE FOR INACTIVATING FUNCTION OF GENE WHICH ENCODES DIACYLGLYCEROL ACYLTRANSFERASE

(75) Inventors: Toyoaki Anai, Saga (JP); Yutaka Takagi, Saga (JP)

(73) Assignee: Saga Prefectural Regional Industry Support Center, Saga-ken (JP)

( * ) Notice: Subject to any disclaimer, the term of this patent is extended or adjusted under 35 U.S.C. 154(b) by 0 days.

(21) Appl. No.: 10/103,247

(22) Filed: Mar. 20, 2002

(65) Prior Publication Data
US 2004/0111762 A1 Jun. 10, 2004

(30) Foreign Application Priority Data
Aug. 28, 2001 (JP) .............................. 2001-258596

(51) Int. Cl.
C12N 15/09 (2006.01)
C12N 15/29 (2006.01)
C12N 15/82 (2006.01)
A01H 5/00 (2006.01)
A01H 5/10 (2006.01)

(52) U.S. Cl. .................. 800/281; 800/285; 800/286; 800/287; 800/298; 800/312; 536/23.1; 536/23.2; 536/23.6

(58) Field of Classification Search ................ 800/278, 800/281, 298, 312, 285, 286, 287; 536/23.1, 536/23.2, 23.6
See application file for complete search history.

(56) References Cited

FOREIGN PATENT DOCUMENTS
WO WO 00/32756 * 6/2000

OTHER PUBLICATIONS

Robbins M. et al, Plant Physiol., 1998; vol. 116: 1133-1144.*
Branch A.D. TIBS, Feb. 1998, pp. 45-50; p. 47 col. 3.*
Waterhouse P. et al., Trends in Plant Sciences, Nov. 1999, vol. 4, No. 11 pp. 452-457.*
Katavic V. et al., Plant Physiology, May 1995; vol. 108, No. 1, pp. 399-409.*
Attached Sequence report.*
Ogita S. et al. Plant Molecular Biology, 2004, vol. 54; pp. 931-941.*
Specific and heritable genetic interference by double-stranded RNA in *Arabidopis thaliana* Chiou-Fen Chang and Elliot M. Meyerowitz PNAS; Apr. 25, 2000;vol. 97,No. 9 pp. 4986-4990.

* cited by examiner

Primary Examiner—Russell P. Kallis
(74) Attorney, Agent, or Firm—Jordan and Hamburg LLP

(57) ABSTRACT

The present invention provides a method of producing diacylglycerol characterized by inactivating the function of a gene which encodes diacylglycerol acyltransferase having the function of enzymatically reacting with diacylglycerol to create triacylglycerol in a seed, so as to allow diacylglycerol to be accumulated in the seed.

2 Claims, 1 Drawing Sheet

METHOD OF PRODUCING DIACYLGLYCEROL AND GENE FOR INACTIVATING FUNCTION OF GENE WHICH ENCODES DIACYLGLYCEROL ACYLTRANSFERASE

FIELD OF THE INVENTION

The present invention relates to a method of producing diacylglycerol according to gene recombination techniques, and a gene for inactivating the function of a gene which encodes diacylglycerol acyltransferase.

BACKGROUND OF THE INVENTION

Diacylglycerol has different nutritive values and physiochemical characteristics from triacylglycerol which is a major component of vegetable oil. Taking advantage of such characteristics, diacylglycerol has a wide range of prospective applications to edible oil, such as a salad oil, or chemical materials.

Heretofore, diacylglycerol has been produced from triacylglycerol obtained by compressing soybeans, rapeseeds or the like. These conventional methods include (1) a method based on an ester exchange reaction between oil and glycerol, and (2) a method based on an esterification reaction using fatty acid and glycerol. In these methods, either one of a chemical reaction using a catalyst of alkali (earth) metal hydroxide or an enzyme reaction has been used (see Japanese Patent Laid-Open Publication No. 2001-64671, WO 99/48378).

Such reactions have a disadvantage in terms of complicated production processes and/or relatively high cost because of (1) the need for a process of separating a desired product from by-products to purifying the desired product or (2) the needs for purified fatty acid as a material.

SUMMARY OF THE INVENTION

In order to improve the complicated production processes and/or relatively high cost in the conventional methods, it is an object of the present invention to provide a method of producing diacylglycerol, capable of directly producing diacylglycerol, which is hardly created from ordinary plants, by genetically modifying a lipid metabolic pathway of a plant, and to provide a gene sequence for inactivating the function of a gene which encodes diacylglycerol acyltransferase.

According to the present invention, there is provided a method of producing diacylglycerol characterized by inactivating the function of a gene which encodes diacylglycerol acyltransferase having the function of enzymatically reacting with diacylglycerol to create triacylglycerol in a seed, so as to allow diacylglycerol to be accumulated in the seed.

For example, in soybeans, all or a part of a diacylglycerol acyltransferase gene having a base sequence as described in claim 2 is used to suppressing the expression of the gene which encodes diacylglycerol acyltransferase having the function of creating triacylglycerol from diacylglycerol in the seed.

PREFERRED EMBODIMENT OF THE INVENTION

Figure 1:
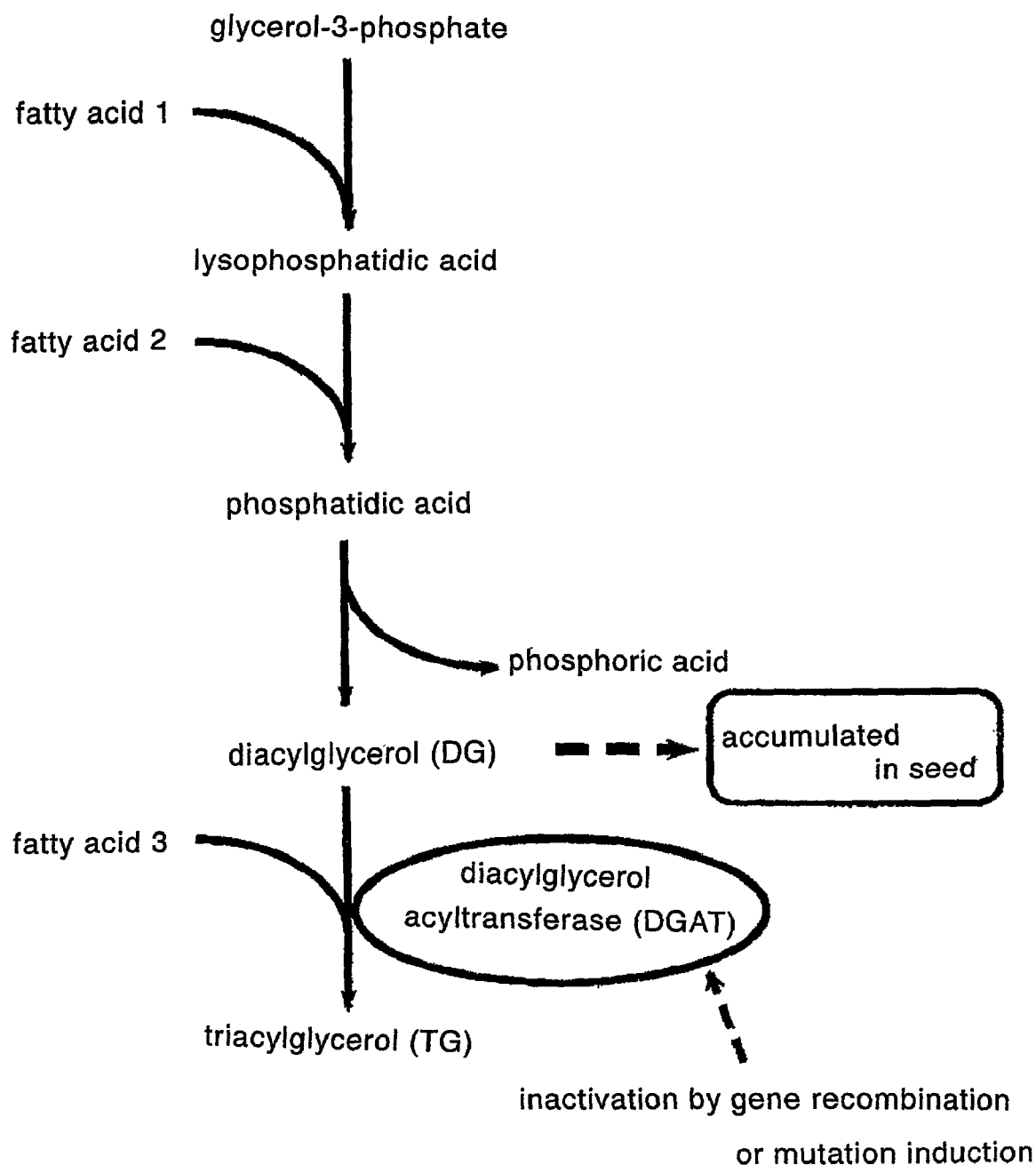
FIG. 1 is an explanatory diagram of a biosynthesis of triacylglycerol.

In an immature seed of a soybean, sesame or the like, triacylglycerol is synthesized from a glycerol-3-phosphate synthesized in cytoplasm during its growth process and a fatty acid synthesized in chloroplast and endoplasmic reticulum, through lysophosphatidic acid, phosphatidic acid, and diacylglycerol, by acylating and dephosphorylating reactions according to enzymes in the so-called Kennedy pathway residing in endoplasmic reticulum membrane, and the synthesized triacylglycerol is eventually accumulated as an oil body in the seed.

Diacylglycerol acyltransferase is an enzyme serving as a catalyst of the final step of the above series of enzymatic reactions or a reaction of transferring an acyl group to diacylglycerol, and it is considered that the catalysis of this enzyme acts as a rate-determining reaction in the biosynthetic pathway of triacylglycerol.

From this point of view, in the present invention, a diacylglycerol acyltransferase gene is recombined to inactivate its function or to suppress its catalytic action, so that diacylglycerol created during the course of synthesizing triacylglycerol is not synthesized as triacylglycerol, but sufficiently accumulated in a seed.

For example, in a soybean which is one of important oil crops, the gene sequence of diacylglycerol acyltransferase was obtained by screening a cDNA library derived from a soybean immature seed with the use of a probe designed based on a base sequence in a diacylglycerol acyltransferase cDNA of *Arabidopsis thaliana*. Further, the gene sequence of diacylglycerol acyltransferase clarified by determining a base sequence in the conventional manner was as described in claim 2. As a result, it was proved that the diacylglycerol acyltransferase gene of a soybean encodes a polypeptide composed of 500 amino acids, and exhibits 59.9% and 62.0% of homology in amino acids level, respectively, with the diacylglycerol acyltransferase of *Arabidopsis thaliana* and the diacylglycerol acyltransferase of Tobacco. Further, by analyzing the expression pattern of the gene encoding diacylglycerol acyltransferase based on the Northern blotting analysis, it was proved that the gene encoding diacylglycerol acyltransferase is highly expressed in an immature seed having a diameter of about 7 to 9 mm, and the expression is induced by an ethylene treatment.

According to the present invention, the original function of the gene encoding diacylglycerol acyltransferase can be inactivated by a gene recombination. The gene can be recombined by using conventional gene recombination techniques based on the development of vectors and the gene transfer.

A cDNA fragment to be transferred may have a full or a partial length. However, it is desirable to use a cDNA fragment derived from a plant seed into which the gene is transferred. The cDNA fragment is linked in the forward or backward direction to a promoter having a strong function in a plant, such as the cauliflower mosaic virus 35S promoter, and is then transferred into a plant by use of a conventional method, such as the Agrobacterium method or the particle gun method. During this process, the type of a tissue into which the gene is transferred is not limited to a specific cultured cell, lamina, growing point or the like, and any suitable tissue having means for obtaining a gene-recombined individual can be used. In addition, a marker for selecting the gene-transferred cell (individual) does not have any specific limitation as in various antibiotics or herbicides, phytohormone synthetic genes or the like.

A conventional technique can be used as the method for developing vectors. In pBI121 as a gene transfer vector for plants, this vector is used for the gene transfer using Agrobacterium, and a T-DNA region existing between an RB site and an LB site of pBI121 is transferred into a plant. A desired gene is generally transferred into a plant by using such a vector. When it is intended to X transfer a diacylglycerol acyltransferase gene, GUS gene may be cut out and the diacylglycerol acyltransferase gene may be integrated as a substitute for the cut-out GUS gene. For the cutting-out and integration, each recognition sequence of restriction enzyme existing at both sides of the GUS gene is used. Further, the transcription of the integrated gene is caused from one of the sides of the GUS gene to the other side, wherein this direction and the opposite direction are defined as forward and backward directions, respectively. The original functions of the plant gene in case of integrating the diacylglycerol acyltransferase gene in the forward direction and the backward direction can be suppressed by the cosuppression method and by the antisense method or RNA interference method, respectively.

The gene transfer is carried out by using a conventional method, such as the Agrobacterium method, particle gun method, or electroporation method. Instead of gene recombination, mutation may be used to obtain the gene for suppressing the original function of the gene which encodes diacylglycerol acyltransferase. A treatment for damaging DNA is performed to induce the mutation. For example, a treatment using nuclear-radiation or chemical mutagen (such as alkylating agent) or a treatment of incorporating nucleic acid analogues is performed to provide a mutant group, and a diacylglycerol accumulating type mutant is selected from the resulting mutant group.

These treatments can cause breakage, deletion or base substitution at an unspecified location of DNA to create a different gene from the original gene.

However, these mutations are caused definitely at random, and thereby the resulting mutations are almost independent of the desired gene. Thus, it is required to pick up a specific desired mutant gene from the mutant group. For example, in soybeans, the desired mutant can be only about one per tens of thousands to hundreds of thousands of individuals. Accordingly, it is necessary to provide a method for detecting a gene mutation efficiently and accurately.

The desired mutant gene can be detected by directly analyzing a base sequence of DNA because the mutations are caused on the DNA. The PCR method or Southern blotting method can be used for analyzing the DNA. Alternatively, the desired mutant gene can be determined by examining mRNA transcribed from the DNA or protein translated from the mRNA because diacylglycerol acyltransferase has the function of an enzyme. The Northern blotting method and the Western blotting method can be used for analyzing the RNA and the protein, respectively.

EXAMPLE

One example of gene recombination in soybeans will be described below.

1. Isolation (Cloning) of a Soybean Diacylglycerol Acyltransferase Gene
   (1) An mRNA is extracted from soybean immature seeds and purified according to a conventional manner.
   (2) Double-stranded cDNAs are synthesized by using the mRNA as a template, and are then integrated into a vector to prepare a cDNA library.
   (3) Using a primer designed based on the base sequence of a known diacylglycerol acyltransferase gene, a PCR is caused in the prepared library to amplify a part of the diacylglycerol acyltransferase gene.
   (4) After determining the base sequence of the gene fragment amplified by the PCR, the cDNA library is screened by using the fragment as a probe to obtain a full-length soybean diacylglycerol acyltransferase gene.

2. Development of an Expression Vector for an Antisense Diacylglycerol Acyltransferase Gene After cutting out a cloned soybean diacylglycerol acyltransferase gene by using a restriction gene, the cloned soybean diacylglycerol acyltransferase gene is linked to an adequate promoter in the backward direction according to a conventional manner to create a plasmid having an arbitrary selection marker gene (preferably, this promoter provides a seed-specific gene expression. However, any other suitable promoter providing a steady gene expression, such as CaMV 35S promoter or actin promoter, may be used).

3. Transfer of an Antisense Gene Into a Soybean Cell.
   (1) The developed vector is coated over golden particles or the like, and the golden particles coated with the vector are transferred into cultured cells of a plant by using a particle gun.
   (2) The gene transfer cells are cultured by using a suitable agent while selecting the cultured cells to obtain a plant body through an adventitious embryo.

According to the present invention, a plant having an inactivated function of a gene which decodes diacylglycerol acyltransferase is used to allow desired diacylglycerol to be obtained immediately after an oil press process. This eliminates any need for the complicated synthesis process and the by-product removal process which have been inevitable in a conventional industrial production method, and thereby provides desirable supply of diacylglycerol with reduced cost and enhanced stability.

Further, the present invention allows lipid metabolic pathway in a plant body to be genetically modified, so as to accumulate a lager amount of diacylglycerol, which is hardly created by ordinary plants, in a seed. Thus, a desired diacylglycerol can be obtained directly from a plant without using any complicated processes as in the conventional method.

In addition, whereas the conventional method has produced diacylglycerol by processing oil/fats obtained through an oil press process and has not thereby been able to modify any oil/fats contained in grains, the present invention can freely change the ratio of triacylglycerol/diacylglycerol and can thereby provide enhanced nutritive value even in crops used directly for food.

What is claimed is:

1. A method of accumulating diacylglycerol in a soybean seed comprising:
    transforming a soybean plant with an RNA interference vector comprising a polynucleotide of SEQ ID NO: 1 in forward and backward orientation operably linked to a soybean seed specific promoter,
    wherein expression of said vector suppresses expression of diacylglycerol acyltransferase in said soybean seed and diacylglycerol accumulates in the seed to an amount larger than in untransformed soybean seed.

2. An isolated soybean diacylglycerol acyltransferase polynucleotide comprising SEQ ID NO: 1, wherein SEQ ID NO: 1 encodes SEQ ID NO: 2.

* * * * *

SEQUENCE LISTING

<160> NUMBER OF SEQ ID NOS: 2

<210> SEQ ID NO 1
<211> LENGTH: 1560
<212> TYPE: DNA
<213> ORGANISM: Glycine max
<220> FEATURE:
<221> NAME/KEY: CDS
<222> LOCATION: (13)..(1518)

<400> SEQUENCE: 1

```
gtcttcttttt cc atg gcg att tcc gat gag cct gaa act gta gcc act gct        51
              Met Ala Ile Ser Asp Glu Pro Glu Thr Val Ala Thr Ala
                1               5                  10 ctc aac cac tct tcc ctg cgc cgc cgt ccc acc gcc gct ggc ctc ttc           99
Leu Asn His Ser Ser Leu Arg Arg Arg Pro Thr Ala Ala Gly Leu Phe
 15              20                  25 aat tcg tcc gag acg acc acc gac agt tcc ggt gat gac ttg gcc aag          147
Asn Ser Ser Glu Thr Thr Thr Asp Ser Ser Gly Asp Asp Leu Ala Lys
 30              35                  40                  45 gat tcc ggt tcc gac gac tcc atc agc agc gac gcc gcc gcc aat tcg          195
Asp Ser Gly Ser Asp Asp Ser Ile Ser Ser Asp Ala Ala Ala Asn Ser
             50                  55                  60 caa ccg caa caa aaa caa gac act gat ttc tcc gtc ctc aaa ttc gcc          243
Gln Pro Gln Gln Lys Gln Asp Thr Asp Phe Ser Val Leu Lys Phe Ala
                 65                  70                  75 tac cgt cct tcc gtc ccc gct cac cgc aaa gtg aag gaa agt ccg ctc          291
Tyr Arg Pro Ser Val Pro Ala His Arg Lys Val Lys Glu Ser Pro Leu
             80                  85                  90 agc tcc gac acc att ttc cgt cag ttg cag agt cac gcg ggc ctc ttc          339
Ser Ser Asp Thr Ile Phe Arg Gln Leu Gln Ser His Ala Gly Leu Phe
         95                 100                 105 aac ctc tgt ata gta gtc ctt gtt gct gtg aac agc aga ctt atc att          387
Asn Leu Cys Ile Val Val Leu Val Ala Val Asn Ser Arg Leu Ile Ile
110                 115                 120                 125 gag aat tta atg aag tat ggt tgg ttg atc aag tat ggc ttt tgg ttt          435
Glu Asn Leu Met Lys Tyr Gly Trp Leu Ile Lys Tyr Gly Phe Trp Phe
                130                 135                 140 agt tca aaa tca ttg aga gat tgg cct ctc ttc atg tgc tgt ctt agt          483
Ser Ser Lys Ser Leu Arg Asp Trp Pro Leu Phe Met Cys Cys Leu Ser
            145                 150                 155 ctt gcc ata ttt cca ctt gct gcc ttt gtt gtg gaa agg ttg gca caa          531
Leu Ala Ile Phe Pro Leu Ala Ala Phe Val Val Glu Arg Leu Ala Gln
        160                 165                 170 caa aag tgt att tct gaa cca gtt gtt gtt cta ctt cat cta ata ata          579
Gln Lys Cys Ile Ser Glu Pro Val Val Val Leu Leu His Leu Ile Ile
    175                 180                 185 tca act gtt gaa ctg tgc tat ccg gtt tta gta ata ctc agg tgt gat          627
Ser Thr Val Glu Leu Cys Tyr Pro Val Leu Val Ile Leu Arg Cys Asp
190                 195                 200                 205 tct gct ttt gta tct ggt gtc acg ttg atg cta tta act tgc att gtg          675
Ser Ala Phe Val Ser Gly Val Thr Leu Met Leu Leu Thr Cys Ile Val
                210                 215                 220 tgg tta aaa ttg gtg tca tat gca cat aca aac tat gat atg aga gca          723
Trp Leu Lys Leu Val Ser Tyr Ala His Thr Asn Tyr Asp Met Arg Ala
            225                 230                 235 ctt act gtt tcg aat gaa aag gga gaa aca tta ccc aat act ttg att          771
Leu Thr Val Ser Asn Glu Lys Gly Glu Thr Leu Pro Asn Thr Leu Ile
        240                 245                 250
```

-continued

| | | |
|---|---|---|
| atg gag tat ccg tac act gtg acc ttc agg agt ttg gca tac ttc atg<br>Met Glu Tyr Pro Tyr Thr Val Thr Phe Arg Ser Leu Ala Tyr Phe Met<br>255                         260                       265 | 819 |

```
atg gag tat ccg tac act gtg acc ttc agg agt ttg gca tac ttc atg      819
Met Glu Tyr Pro Tyr Thr Val Thr Phe Arg Ser Leu Ala Tyr Phe Met
255                 260                 265 gtt gct cct aca tta tgc tat cag aca agc tat cct cgc aca cct tca      867
Val Ala Pro Thr Leu Cys Tyr Gln Thr Ser Tyr Pro Arg Thr Pro Ser
270                 275                 280                 285 gtt cga aag ggt tgg gtg ttt cgt caa ctt gtc aag ctg ata ata ttt      915
Val Arg Lys Gly Trp Val Phe Arg Gln Leu Val Lys Leu Ile Ile Phe
                290                 295                 300 aca gga gtt atg gga ttt ata ata gaa caa tat atg aat cct att gta      963
Thr Gly Val Met Gly Phe Ile Ile Glu Gln Tyr Met Asn Pro Ile Val
            305                 310                 315 caa aac tca act cat cct ttg aag gga aac ctt cta tat gcc att gag     1011
Gln Asn Ser Thr His Pro Leu Lys Gly Asn Leu Leu Tyr Ala Ile Glu
        320                 325                 330 aga att ctg aag ctt tct gtc cca aat gta tat gtg tgg ctc tgc atg     1059
Arg Ile Leu Lys Leu Ser Val Pro Asn Val Tyr Val Trp Leu Cys Met
335                 340                 345 ttc tac tgc ttt ttc cac ctt tgg tta aat ata ctt gca gag ctt gtt     1107
Phe Tyr Cys Phe Phe His Leu Trp Leu Asn Ile Leu Ala Glu Leu Val
350                 355                 360                 365 cga ttt ggt gat cgt gag ttc tat aaa gat tgg tgg aat gcc aaa act     1155
Arg Phe Gly Asp Arg Glu Phe Tyr Lys Asp Trp Trp Asn Ala Lys Thr
                370                 375                 380 gtt gaa gag tat tgg aag atg tgg aat atg cct gtg cac aaa tgg atg     1203
Val Glu Glu Tyr Trp Lys Met Trp Asn Met Pro Val His Lys Trp Met
            385                 390                 395 gtt cgc cac ata tat ttt cca tgc cta agg cgt ggt ata ccc aag ggt     1251
Val Arg His Ile Tyr Phe Pro Cys Leu Arg Arg Gly Ile Pro Lys Gly
        400                 405                 410 gct gct cca tta att gca ttc ctg gtt tct gct gtg ttt cat gag tta     1299
Ala Ala Pro Leu Ile Ala Phe Leu Val Ser Ala Val Phe His Glu Leu
415                 420                 425 tgc att gcc gtt cct tgc cac atg ttc aag ttg tgg gct ttt ata gga     1347
Cys Ile Ala Val Pro Cys His Met Phe Lys Leu Trp Ala Phe Ile Gly
430                 435                 440                 445 att atg ttt cag gtt cct ttg gtc ttg atc act aat tac ctc caa aat     1395
Ile Met Phe Gln Val Pro Leu Val Leu Ile Thr Asn Tyr Leu Gln Asn
                450                 455                 460 aaa tac aga aac tca atg gtt gga aat atg att ttt tgg ttc ata ttt     1443
Lys Tyr Arg Asn Ser Met Val Gly Asn Met Ile Phe Trp Phe Ile Phe
            465                 470                 475 tgt att ctt ggt caa cca atg agc gta cta ttg tac tac cat gac ttg     1491
Cys Ile Leu Gly Gln Pro Met Ser Val Leu Leu Tyr Tyr His Asp Leu
        480                 485                 490 atg aat aga aaa gga gaa gtt gac taa ggtagcatta cactgttcat           1538
Met Asn Arg Lys Gly Glu Val Asp
495                 500 gtggatgagc ttttgcgttt tc                                             1560
```

<210> SEQ ID NO 2
<211> LENGTH: 501
<212> TYPE: PRT
<213> ORGANISM: Glycine max

<400> SEQUENCE: 2

```
Met Ala Ile Ser Asp Glu Pro Glu Thr Val Ala Thr Ala Leu Asn His
1               5                   10                  15

Ser Ser Leu Arg Arg Arg Pro Thr Ala Ala Gly Leu Phe Asn Ser Ser
            20                  25                  30
```

-continued

```
Glu Thr Thr Thr Asp Ser Ser Gly Asp Asp Leu Ala Lys Asp Ser Gly
         35                  40                  45

Ser Asp Asp Ser Ile Ser Ser Asp Ala Ala Asn Ser Gln Pro Gln
 50                  55                  60

Gln Lys Gln Asp Thr Asp Phe Ser Val Leu Lys Phe Ala Tyr Arg Pro
 65                  70                  75                  80

Ser Val Pro Ala His Arg Lys Val Lys Glu Ser Pro Leu Ser Ser Asp
                 85                  90                  95

Thr Ile Phe Arg Gln Leu Gln Ser His Ala Gly Leu Phe Asn Leu Cys
                100                 105                 110

Ile Val Val Leu Val Ala Val Asn Ser Arg Leu Ile Ile Glu Asn Leu
            115                 120                 125

Met Lys Tyr Gly Trp Leu Ile Lys Tyr Gly Phe Trp Phe Ser Ser Lys
        130                 135                 140

Ser Leu Arg Asp Trp Pro Leu Phe Met Cys Cys Leu Ser Leu Ala Ile
145                 150                 155                 160

Phe Pro Leu Ala Ala Phe Val Val Glu Arg Leu Ala Gln Gln Lys Cys
                165                 170                 175

Ile Ser Glu Pro Val Val Leu Leu His Leu Ile Ile Ser Thr Val
            180                 185                 190

Glu Leu Cys Tyr Pro Val Leu Val Ile Leu Arg Cys Asp Ser Ala Phe
        195                 200                 205

Val Ser Gly Val Thr Leu Met Leu Leu Thr Cys Ile Val Trp Leu Lys
    210                 215                 220

Leu Val Ser Tyr Ala His Thr Asn Tyr Asp Met Arg Ala Leu Thr Val
225                 230                 235                 240

Ser Asn Glu Lys Gly Glu Thr Leu Pro Asn Thr Leu Ile Met Glu Tyr
                245                 250                 255

Pro Tyr Thr Val Thr Phe Arg Ser Leu Ala Tyr Phe Met Val Ala Pro
            260                 265                 270

Thr Leu Cys Tyr Gln Thr Ser Tyr Pro Arg Thr Pro Ser Val Arg Lys
        275                 280                 285

Gly Trp Val Phe Arg Gln Leu Val Lys Leu Ile Ile Phe Thr Gly Val
    290                 295                 300

Met Gly Phe Ile Ile Glu Gln Tyr Met Asn Pro Ile Val Gln Asn Ser
305                 310                 315                 320

Thr His Pro Leu Lys Gly Asn Leu Leu Tyr Ala Ile Glu Arg Ile Leu
                325                 330                 335

Lys Leu Ser Val Pro Asn Val Tyr Val Trp Leu Cys Met Phe Tyr Cys
            340                 345                 350

Phe Phe His Leu Trp Leu Asn Ile Leu Ala Glu Leu Val Arg Phe Gly
        355                 360                 365

Asp Arg Glu Phe Tyr Lys Asp Trp Trp Asn Ala Lys Thr Val Glu Glu
    370                 375                 380

Tyr Trp Lys Met Trp Asn Met Pro Val His Lys Trp Met Val Arg His
385                 390                 395                 400

Ile Tyr Phe Pro Cys Leu Arg Arg Gly Ile Pro Lys Gly Ala Ala Pro
                405                 410                 415

Leu Ile Ala Phe Leu Val Ser Ala Val Phe His Glu Leu Cys Ile Ala
            420                 425                 430

Val Pro Cys His Met Phe Lys Leu Trp Ala Phe Ile Gly Ile Met Phe
        435                 440                 445
```

-continued

```
Gln Val Pro Leu Val Leu Ile Thr Asn Tyr Leu Gln Asn Lys Tyr Arg
    450                 455                 460

Asn Ser Met Val Gly Asn Met Ile Phe Trp Phe Ile Phe Cys Ile Leu
465                 470                 475                 480

Gly Gln Pro Met Ser Val Leu Leu Tyr Tyr His Asp Leu Met Asn Arg
                485                 490                 495

Lys Gly Glu Val Asp
            500
```